United States Patent
Kawamura et al.

(10) Patent No.: US 12,157,720 B2
(45) Date of Patent: Dec. 3, 2024

(54) METHOD FOR PRODUCING UNSATURATED ALDEHYDE

(71) Applicant: NIPPON KAYAKU KABUSHIKI KAISHA, Tokyo (JP)

(72) Inventors: Tomoyuki Kawamura, Yamaguchi (JP); Ryota Hiraoka, Yamaguchi (JP); Shogo Yasuda, Yamaguchi (JP)

(73) Assignee: NIPPON KAYAKU KABUSHIKI KAISHA, Tokyo (JP)

( * ) Notice: Subject to any disclaimer, the term of this patent is extended or adjusted under 35 U.S.C. 154(b) by 610 days.

(21) Appl. No.: 17/437,250

(22) PCT Filed: Mar. 17, 2020

(86) PCT No.: PCT/JP2020/011774
§ 371 (c)(1),
(2) Date: Sep. 8, 2021

(87) PCT Pub. No.: WO2020/203266
PCT Pub. Date: Oct. 8, 2020

(65) Prior Publication Data
US 2022/0169587 A1 Jun. 2, 2022

(30) Foreign Application Priority Data
Mar. 29, 2019 (JP) .................... 2019-065494

(51) Int. Cl.
| | |
|---|---|
| C07C 45/35 | (2006.01) |
| B01J 23/00 | (2006.01) |
| B01J 23/887 | (2006.01) |
| B01J 35/40 | (2024.01) |
| B01J 35/51 | (2024.01) |
| B01J 37/00 | (2006.01) |
| B01J 37/04 | (2006.01) |
| B01J 37/08 | (2006.01) |

(52) U.S. Cl.
CPC ............. *C07C 45/35* (2013.01); *B01J 23/002* (2013.01); *B01J 23/887* (2013.01); *B01J 23/8876* (2013.01); *B01J 35/40* (2024.01); *B01J 35/51* (2024.01); *B01J 37/0018* (2013.01); *B01J 37/0045* (2013.01); *B01J 37/04* (2013.01); *B01J 37/088* (2013.01); *B01J 2523/00* (2013.01)

(58) Field of Classification Search
CPC .................. C07C 45/34; C07C 45/35
See application file for complete search history.

(56) References Cited

U.S. PATENT DOCUMENTS

| | | | |
|---|---|---|---|
| 5,821,390 A | 10/1998 | Ruppel et al. | |
| 6,028,220 A | 2/2000 | Wada et al. | |
| 9,580,376 B2 | 2/2017 | Kawamura et al. | |
| 2001/0021789 A1 | 9/2001 | Tanimoto | |
| 2002/0007088 A1 | 1/2002 | Tanimoto et al. | |
| 2003/0060659 A1 | 3/2003 | Yunoki | |
| 2003/0191343 A1 | 10/2003 | Yunoki et al. | |
| 2003/0191344 A1 | 10/2003 | Yunoki et al. | |
| 2005/0090695 A1 | 4/2005 | Nakamura et al. | |
| 2006/0004226 A1 | 1/2006 | Machhammer et al. | |
| 2006/0004227 A1 | 1/2006 | Dieterle et al. | |
| 2006/0004229 A1 | 1/2006 | Dieterle et al. | |
| 2010/0298601 A1 | 11/2010 | Choi et al. | |
| 2011/0178334 A1 | 7/2011 | Tanimoto et al. | |
| 2012/0245365 A1 | 9/2012 | Wolk et al. | |
| 2013/0310604 A1 | 11/2013 | Kurakami et al. | |
| 2016/0059218 A1 | 3/2016 | Nakazawa et al. | |
| 2016/0145180 A1 | 5/2016 | Kawamura et al. | |
| 2016/0185698 A1 | 6/2016 | Zhao et al. | |

(Continued)

FOREIGN PATENT DOCUMENTS

| | | |
|---|---|---|
| CN | 1448380 | 10/2003 |
| CN | 1697794 | 11/2005 |

(Continued)

OTHER PUBLICATIONS

Extended European Search Report issued Dec. 6, 2022 in corresponding European Patent Application No. 20783026.6.

(Continued)

*Primary Examiner* — Medhanit W Bahta
(74) *Attorney, Agent, or Firm* — WENDEROTH, LIND & PONACK, L.L.P.

(57) ABSTRACT

Provided is a method for producing an unsaturated aldehyde including subjecting an alkene to partial oxidation using a fixed bed multi-tube reactor to produce the corresponding unsaturated aldehyde, in which n catalyst layers (n is 2 or more) in a gas flow direction in a reaction tube are provided, when a filling length of the catalyst layers from a first catalyst layer to an (n−1)th catalyst layer from a gas inlet side of the reaction tube is L, and a filling length of an nth catalyst layer from the gas inlet side of the reaction tube is Ln, a relationship between L and Ln satisfies the following equation (1):

$$1 < L/Ln \leq 3, \tag{1}$$

and
a composition of a catalytically active component contained in the catalyst layers from the first catalyst layer to the (n−1)th layer from the gas inlet side of the reaction tube is different from a composition of a catalytically active component contained in the nth catalyst layer from the gas inlet side of the reaction tube.

6 Claims, No Drawings

(56) References Cited

U.S. PATENT DOCUMENTS

2017/0260118 A1* 9/2017 Mimura .............. B01J 23/888
2018/0029018 A1 2/2018 Kawamura et al.
2018/0186712 A1 7/2018 Sugiyama et al.

FOREIGN PATENT DOCUMENTS

| CN | 101918126 | 12/2010 |
|---|---|---|
| CN | 102596385 | 7/2012 |
| CN | 103772172 | 5/2014 |
| CN | 105801394 | 7/2016 |
| EP | 3 321 247 | 5/2018 |
| JP | 8-3093 | 1/1996 |
| JP | 8-92147 | 4/1996 |
| JP | 10-168003 | 6/1998 |
| JP | 2001-226302 | 8/2001 |
| JP | 2001-328951 | 11/2001 |
| JP | 2003-146920 | 5/2003 |
| JP | 2003-164763 | 6/2003 |
| JP | 2004-2209 | 1/2004 |
| JP | 2005-320315 | 11/2005 |
| JP | 2008-504310 | 2/2008 |
| JP | 2012-176938 | 9/2012 |
| WO | 2014/181839 | 11/2014 |
| WO | 2016/136882 | 9/2016 |
| WO | 2017/010159 | 1/2017 |

OTHER PUBLICATIONS

Notification of First Office Action issued Mar. 23, 2023 in corresponding Chinese Patent Application No. 202080021146.8, with English language translation.
Notice of Reasons for Refusal issued Nov. 6, 2020 in Japanese Application No. 2020-549710 with English translation.
Notice of Reasons for Refusal issued Feb. 8, 2021 in Japanese Application No. 2020-549710 with English translation.
Notice of Reasons for Refusal issued May 11, 2021 in Japanese Application No. 2020-549710 with English translation.
International Search Report issued Jun. 23, 2020 in International (PCT) Application No. PCT/JP2020/011774.
Office Action issued Jan. 18, 2024 in corresponding Japanese patent application No. 2021-101329, with English translation, 6 pages.

* cited by examiner

METHOD FOR PRODUCING UNSATURATED ALDEHYDE

TECHNICAL FIELD

The present invention relates to a method for subjecting an alkene to gas phase catalytic oxidation with molecular oxygen or a molecular oxygen-containing gas to produce the corresponding unsaturated aldehyde.

BACKGROUND ART

Methods for using, as a raw material, an alkene or an alcohol that can be converted into an alkene by an intramolecular dehydration reaction to produce the corresponding unsaturated aldehyde are widely carried out industrially. Among these, many proposals have been made on a catalyst for synthesizing acrolein by subjecting propylene to gas phase catalytic oxidation with molecular oxygen.

With respect to the gas phase oxidation reaction, the yield is most emphasized from the viewpoint of productivity. For improvement of the component of the catalyst composition, Patent Literature 1 describes a technique relating to an atomic proportion of iron, cobalt and nickel, Patent Literature 2 describes a technique relating to an atomic ratio of iron to cobalt and/or nickel, and Patent Literature 3 describes a technique relating to an atomic ratio of nickel to bismuth, an atomic ratio of nickel to an alkali metal component, and an atomic ratio of bismuth to an alkali metal component, in addition to optimizing the atomic ratio of each element to molybdenum. Further, Patent Literature 4 describes an improvement in a composition of bismuth to molybdenum.

This reaction system proceeds with intense heat generated, and this cause a serious problem that local high temperature parts (hot spots) occur in a catalyst layer. The hot spots widely mean a maximum value of the temperature inside the catalyst layer, and usually occur in the catalyst layer on a gas inlet side where the concentration of a raw material is high, and can also occur in a highly active catalyst layer located on a gas outlet side due to deactivation of the catalyst on the inlet side, sudden disturbance factors, and variations in various conditions. The disturbance factor here refers to, for example, a change in flow rate of a heat medium supplied to a reaction bath jacket or a fluctuation in flow amount of the raw material gas due to the air temperature.

The occurrence of hot spots leads to shortening the life of the catalyst, and reducing the yield due to an excessive oxidation reaction, and sometimes leads to a runaway reaction. Therefore, several techniques have been proposed to control the activity of the catalyst filled in a portion where a hot spot occurs, in order to control the temperature of the hot spot.

For example, Patent Literature 5 discloses a technique of decreasing the temperature of the hot spot by using a catalyst whose activity is adjusted by changing a carrying amount, and by using a catalyst whose activity is adjusted by changing a calcination temperature of the catalyst. Patent Literature 6 discloses a technique of using a catalyst whose activity is adjusted by changing a ratio of an apparent density of the catalyst. Patent Literature 7 discloses a technique of using a catalyst whose activity is adjusted by changing a content of an inert component in a catalyst molded body, and by changing an occupied volume of the catalyst molded body, the type and/or amount of an alkali metal, and the calcination temperature of the catalyst. Patent Literature 8 discloses a technique that a reaction zone in which the occupied volume of the catalyst molded body is changed is provided and an inert substance is mixed in at least one reaction zone. Patent Literature 9 discloses a technique of using a catalyst whose activity is adjusted by changing a calcination temperature of the catalyst. Patent Literature 10 discloses a technology of using a catalyst whose activity is adjusted by changing the occupied volume of the catalyst and the calcination temperature and/or the type and amount of the alkali metal.

CITATION LIST

Patent Literature

Patent Literature 1: JP-A-2003-164763
Patent Literature 2: JP-A-2003-146920
Patent Literature 3: WO 2014/181839
Patent Literature 4: WO 2016/136882
Patent Literature 5: JP-A-H10-168003
Patent Literature 6: JP-A-2004-002209
Patent Literature 7: JP-A-2001-328951
Patent Literature 8: JP-A-2005-320315
Patent Literature 9: JP-A-H08-3093
Patent Literature 10: JP-A-2001-226302

SUMMARY OF INVENTION

Technical Problem

However, it cannot be said that improvement of the yield by the above means results in the sufficient yield of a target product. The amount of alkene required for production is influenced and the production cost is greatly influenced by the above means. Therefore, an improvement is required. In addition, continuing an operation in which a target compound is gained at a low yield causes to generate a large amount of by-products, and thus a large burden is applied in a refining step to cause a problem that the time and the operating cost required for the refining step increase. Further, depending on the type of the by-products, the by-products may be deposited on the surface of the catalyst or in a gas flow path near the catalyst. They cover necessary reaction active sites on the surface of the catalyst to reduce the activity of the catalyst, and thus it is necessary to forcibly increase the activity and it is inevitable to raise a temperature of a reaction bath. Then, the catalyst is subjected to thermal stress, and this causes a decrease in life and selectivity. As a result, a further decrease in yield is also caused.

Furthermore, measures for stable operation such as prevention of hot spots are not yet sufficient. For example, in an industrial plant, variations in heat removal capacity derived from a reactor structure, horizontal and vertical distributions of the heat medium temperature, and a distribution of a gas flow rate for each reaction tube may occur. It is almost impossible to use the catalyst in the same state in all reaction tubes.

When the catalyst used in the industrial plant is analyzed, a reaction tube where the catalyst at a gas inlet for a raw material is intensively deteriorated and a reaction tube where the catalyst is moderately deteriorated throughout may be found. More surprisingly, a reaction tube where the catalyst at a gas outlet for a raw material is more deteriorated than the catalyst at the inlet may be also found. This suggests that the temperature of the hot spot of the catalyst layer on the side of the gas outlet for a raw material may have been abnormally high, and in some cases, a runaway reaction may occur. It is considered that this is because conversion rates of raw material hydrocarbons and the shape of the temperature distribution vary, due to the above-described variations in reaction tube diameter in the industrial plant, variations in heat removal capacity derived from the reactor structure, horizontal and vertical distributions of the heat medium temperature and the distribution of the gas flow rate for each reaction tube. The problem to be solved is to develop a technique that allows the reaction to be maintained more safely, stably and for a long period of time even when various factors of variation occur at the same time. When a plant shutdown occurs due to reaction abnormality, the loss derived from unproduced parts during this period may occur and the life of the catalyst may be shortened depending on abnormal temperature or atmosphere. When a runaway reaction occurs, a great loss such as damage to the industrial plant equipment or an accident may occur. As described above, an improvement in both yield and stable operation is desired.

As a conventional production technique, a multi-layer filling method is adopted in which a catalyst having low activity is used on a gas inlet side of the reaction tube, a catalyst having high activity is used on a gas outlet side of the reaction tube, and a filling length of the catalyst layer near the gas outlet side is longer than that on the gas inlet side.

In order to deal with the above circumstances and problems, the present inventors have made intensive investigations. As a result, the present inventors have focused on the point that when the reaction is carried out in a filling having a catalyst layer divided into two or more layers, a selectivity of a target product of the catalyst layer having low activity located on the gas inlet side of the reaction tube is particularly high. Then, they have found that making the filling length of the catalyst layer on the gas inlet side of the reaction tube longer than the filling length of the catalyst layer having high activity located on the gas outlet side of the reaction tube and making compositions of catalytically active components between specific catalyst layers different increase the selectivity of an unsaturated aldehyde, and in addition, controlling an occupancy of the catalyst having high activity located on the outlet side makes it easier to prevent the runaway reaction that may occur due to variations in various reaction conditions and disturbance factors and these allow for a more stable plant operation in which the yield is higher.

Solution to Problem

That is, the present invention relates to the following 1) to 7).
1) A method for producing an unsaturated aldehyde comprising,
subjecting an alkene to partial oxidation using a fixed bed multi-tube reactor to produce the corresponding unsaturated aldehyde,
wherein n catalyst layers (n is 2 or more) in a gas flow direction in a reaction tube are provided,
when a filling length of the catalyst layers from a first catalyst layer to an (n−1)th catalyst layer from a gas inlet side of the reaction tube is L, and a filling length of an nth catalyst layer from the gas inlet side of the reaction tube is Ln, a relationship between L and Ln satisfies the following equation (1):

$$1 < L/Ln \leq 3, \tag{1}$$

and
a composition of a catalytically active component contained in the catalyst layers from the first catalyst layer to the (n−1)th layer from the gas inlet side of the reaction tube is different from a composition of a catalytically active component contained in the nth catalyst layer from the gas inlet side of the reaction tube.
2) The method for producing an unsaturated aldehyde described in 1), wherein the relationship between L and Ln satisfies the following equation (2):

$$1.1 < L/Ln \leq 1.4. \tag{2}$$

3) The method for producing an unsaturated aldehyde described in 1) or 2), wherein a catalyst contained in the catalyst layer has a spherical shape.
4) The method for producing an unsaturated aldehyde described in any one of 1) to 3), wherein a concentration of the alkene in a raw material is 6 vol % to 12 vol %.
5) The method for producing an unsaturated aldehyde described in any one of 1) to 4), wherein each catalyst layer in the reaction tube contains a catalyst containing a catalytically active component having a composition represented by the following formula (3):

$$Mo_{12}Bi_aFe_bCo_cNi_dX_eY_fZ_gO_h \tag{3}$$

where X is at least one element selected from the group consisting of magnesium (Mg), calcium (Ca), manganese (Mn), copper (Cu), zinc (Zn), cerium (Ce) and samarium (Sm), Y is at least one element selected from the group consisting of boron (B), phosphorus (P), arsenic (As), antimony (Sb) and tungsten (W), Z is at least one element selected from the group consisting of sodium (Na), potassium (K), rubidium (Rb) and cesium (Cs), (a) to (g) represent an atomic proportion of each component, h is a numerical value determined by a degree of oxidation of a catalyst component, a=0.40 to 2.0, b=1 to 3, c=3 to 7.5, d=2 to 4, e=0 to 10, f=0 to 10, g=0.01 to 0.50, h is a numerical value for satisfying oxidation states of the other elements, d/a is 1 or more and 9 or less, d/g is 5 or more and 350 or less, and a/g is 0.8 or more and 90 or less.
6) The method for producing an unsaturated aldehyde described in any one of 1) to 5), wherein a catalyst contained in the nth catalyst layer is not diluted with an inert substance.
7) The method for producing an unsaturated aldehyde described in any one of 1) to 6), wherein a catalyst contained in the catalyst layer is a carried catalyst.

Advantageous Effects of Invention

The present invention allows for safely and stably maintaining a high yield for a long period of time in an industrial plant, in the case of using, as a raw material, an alkene or an alcohol that can be converted into an alkene by an intramolecular dehydration reaction to produce the corresponding unsaturated aldehyde.

DESCRIPTION OF EMBODIMENTS

[Relationship Between Ln and L]

The present invention mainly relates to a filling length of a catalyst layer. The filling length of the catalyst layer is defined as follows.

Ln: the filling length of an nth layer from a gas inlet side of the reaction tube when the n catalyst layers are provided by being divided by n in a gas flow direction in a reaction tube L: the filling length of the catalyst layers from the first catalyst layer to an (n−1)th catalyst layer from the gas inlet side of the reaction tube In the present invention, a relationship between Ln and L has a relationship represented by the above equation (1). In addition, a composition of a catalytically active component contained in the catalyst layers from the first catalyst layer to the (n−1)th layer from the gas inlet side of the reaction tube is different from a composition of a catalytically active component contained in the nth catalyst layer from the gas inlet side of the reaction tube. This enables the selectivity of an unsaturated aldehyde to increase, furthermore, makes it easier to prevent a runaway reaction that may occur due to variations in reaction conditions and disturbances, and achieves a safer and more stable plant operation in which the yield is higher. When the runaway reaction is prevented, it is expected that the thermal stress of the catalyst can be prevented and the life can be extended.

The above equation (2) is obtained by limiting the above equation (1) to a preferred range.

Too small value of L/Ln fails to achieve a sufficient selectivity. Too large value of L/Ln makes it difficult to keep a reaction bath temperature low within a normal range. As a result, a reaction bath temperature is required to be high, and the selectivity may decrease.

The lower limit of L/Ln is a value larger than 1. Further, the lower limit of L/Ln is more preferably a value larger than 1.05, and particularly preferably a value larger than 1.1. The upper limit thereof is 3. A more preferred upper limit is 2, a still more preferred upper limit is 1.5, and a particularly preferred upper limit is 1.4. Therefore, the most preferred range for the value of L/Ln is larger than 1.1 and 1.4 or less.

In catalytically active components contained in the catalyst layer used in the present invention, the catalytically active components contained in the catalyst layers from the first layer to the (n−1)th layer have different compositions from the catalytically active components contained in the nth catalyst layer, as described above. In particular, from the viewpoint of catalytic activity, the nth catalyst layer, which is a catalyst layer (bottom layer) located closest to the gas outlet side of the reaction tube, preferably contains a catalytically active component containing potassium (K), and the catalyst layers from the first layer to the (n−1)th layer preferably contain a catalytically active component containing cesium (Cs).

As a specific composition of the catalytically active component, the following catalytically active components can be exemplified.

Catalyst

The catalytically active component contained in an upper layer (the catalyst layers from the first layer to the (n−1)th layer from the gas inlet side of the reaction tube) used in the present invention is preferably a catalytically active component of a composite metal oxide represented by the following formula (3).

 (3)

In the above formula (3), X is at least one element selected from the group consisting of magnesium (Mg), calcium (Ca), manganese (Mn), copper (Cu), zinc (Zn), cerium (Ce) and samarium (Sm), Y is at least one element selected from the group consisting of boron (B), phosphorus (P), arsenic (As), antimony (Sb) and tungsten (W), Z is at least one element selected from the group consisting of sodium (Na), potassium (K), rubidium (Rb) and cesium (Cs), (a) to (g) represent an atomic proportion of each component, h is a numerical value determined by a degree of oxidation of a catalyst component, a=0.40 to 2.0, b=1 to 3, c=3 to 7.5, d=2 to 4, e=0 to 10, f=0 to 10, g=0.01 to 0.50, h is a numerical value for satisfying oxidation states of the other elements, d/a is 1 or more and 9 or less, d/g is 5 or more and 350 or less, and a/g is 0.8 or more and 90 or less.

In the present application, "to" means or more and or less, that is, the numerical values sandwiching "to" are included.

The above X is preferably at least one element selected from the group consisting of magnesium (Mg), calcium (Ca), manganese (Mn), zinc (Zn), and cerium (Ce), more preferably at least one element selected from the group consisting of magnesium (Mg), calcium (Ca), zinc (Zn) and cerium (Ce), and particularly preferably at least one element selected from the group consisting of magnesium (Mg), calcium (Ca) and cerium (Ce).

The above Y is preferably at least one element selected from the group consisting of boron (B), phosphorus (P), antimony (Sb) and tungsten (W), more preferably at least one element selected from the group consisting of phosphorus (P), antimony (Sb) and tungsten (W), and particularly preferably at least one element selected from the group consisting of antimony (Sb) and tungsten (W).

The above Z is preferably at least one element selected from the group consisting of potassium (K), rubidium (Rb), and cesium (Cs), more preferably at least one element selected from the group consisting of potassium (K) and cesium (Cs), and particularly preferably cesium (Cs).

For the above a, the preferred upper limit is 1.7, the more preferred upper limit is 1.5, and the particularly preferred upper limit is 1.2. The preferred lower limit is 0.5, the more preferred lower limit is 0.6, and the particularly preferred lower limit is 0.7.

For the above b, the preferred upper limit is 2.8, the more preferred upper limit is 2.5, and the particularly preferred upper limit is 2.3. The preferred lower limit is 1.5, the more preferred lower limit is 1.6, and the particularly preferred lower limit is 1.8.

For the above c, the preferred upper limit is 7.3, the more preferred upper limit is 7.2, and the particularly preferred upper limit is 7.0. The preferred lower limit is 4.0, the more preferred lower limit is 5.0, and the particularly preferred lower limit is 6.0.

For the above d, the preferred upper limit is 3.8, the more preferred upper limit is 3.5, and the particularly preferred upper limit is 3.3. The preferred lower limit is 2.1, the more preferred lower limit is 2.2, and the particularly preferred lower limit is 2.3.

For the above e, the preferred upper limit is 8.0, the more preferred upper limit is 5.0, and the particularly preferred upper limit is 3.0. The preferred lower limit is 0.

For the above f, the preferred upper limit is 8.0, the more preferred upper limit is 5.0, and the particularly preferred upper limit is 3.0. The preferred lower limit is 0.

For the above g, the preferred upper limit is 0.3, and the particularly preferred upper limit is 0.2, and the particularly preferred upper limit is 0.1. The preferred lower limit is 0.015, the more preferred lower limit is 0.02, and the particularly preferred lower limit is 0.03.

For the above d/a, the preferred upper limit is 7.5, the more preferred upper limit is 5.7, and the particularly preferred upper limit is 4.8. The preferred lower limit is 1.3, the more preferred lower limit is 1.5, and the particularly preferred lower limit is 2.0.

For the above d/g, the preferred upper limit is 230, the more preferred upper limit is 160, and the particularly preferred upper limit is 110. The preferred lower limit is 8, the more preferred lower limit is 14, and the particularly preferred lower limit is 24.

For the above a/g, the preferred upper limit is 85, the more preferred upper limit is 70, and the particularly preferred upper limit is 35. The preferred lower limit is 1.8, the more preferred lower limit is 4.0, and the particularly preferred lower limit is 8.0.

The catalytically active component contained in a lower layer (the nth catalyst layer from the gas inlet side of the reaction tube when the n catalyst layers are provided in the gas flow direction in the reaction tube) used in the present invention is not limited, but is preferably represented by the above formula (3). That is, a preferred embodiment of the present invention is an embodiment in which the catalytically active component contained in all the catalyst layers in the reaction tube is a catalytically active component having a composition represented by the above formula (3).

When the catalytically active component having a composition represented by the above formula (3) is used in the lower layer, the above z is preferably at least one element selected from the group consisting of potassium, rubidium, and cesium, more preferably at least one element selected from the group consisting of potassium and cesium, and particularly preferably potassium.

In addition, X, Y, a, b, c, d, e, f, g, d/a, d/g, and a/g are the same as those in the above formula (3), including the preferred ones.

More specifically, a catalytically active component represented by the following formula (3-1) is preferably contained in the upper layer and/or a catalytically active component represented by the following formula (3-2) is preferably contained in the lower layer. A composition of the catalytically active component represented by the following formula (3-1) contained in the upper layer and a composition of the catalytically active component represented by the following formula (3-2) contained in the lower layer are different from each other.

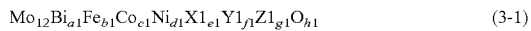

$$Mo_{12}Bi_{a1}Fe_{b1}Co_{c1}Ni_{d1}X1_{e1}Y1_{f1}Z1_{g1}O_{h1} \qquad (3\text{-}1)$$

In the above formula (3-1), X1, Y1, (a1) to (h1) are defined in the same manner as the X, Y and (a) to (h) defined in the above formula (3), Z1 is potassium (K) or cesium (Cs), and preferably Z1 is cesium (Cs).

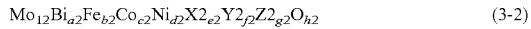

$$Mo_{12}Bi_{a2}Fe_{b2}Co_{c2}Ni_{d2}X2_{e2}Y2_{f2}Z2_{g2}O_{h2} \qquad (3\text{-}2)$$

In the above formula (3-2), X2, Y2, (a2) to (h2) are defined in the same manner as the X, Y and (a) to (h) defined in the above formula (3), Z2 is potassium (K) or cesium (Cs), and preferably Z2 is potassium (K).

The shape of the catalyst contained in the catalyst layer used in the present invention is not limited, but a spherical shape, a columnar shape, a ring shape, a powder shape, or the like can be used, and a spherical shape is particularly preferred.

In the case of filling a catalyst with two layers, both the catalyst contained in the upper layer and the catalyst contained in the lower layer may be diluted with an inert substance, but a method in which neither the catalyst contained in the upper layer nor the lower layer is diluted is more preferred.

In the case of providing three or more (n≥3) catalyst layers, the catalytically active component used for the catalyst layers other than the first layer and the nth layer (hereinafter referred to as a middle layer) may be a catalytically active component of a composite metal oxide represented by the above formula (3) or a catalyst having a composition completely different therefrom, but is preferably the composite metal oxide catalyst represented by the above formula (3). In this case, the middle layer can be formed by changing a dilution ratio with the inert substance, if necessary. It is preferable to use the catalytically active component represented by the above formula (3-1) in the upper layer and the middle layer, and to use the catalytically active component represented by the above formula (3-2) in the lower layer. The number of catalyst layers of the present invention is preferably two or three, and particularly preferably two.

The preferred range of the dilution ratio using the inert substance is described below. The dilution ratio referred to here is a numerical value indicating the mass ratio of the catalyst occupied in the catalyst layer composed of the catalyst and the inert substance. For example, that the catalyst layer is diluted to 80 mass % means that the catalyst is 80 mass % and the inert substance is 20 mass %. As described in a method for producing a catalyst later, when the catalytically active component is carried on an inert carrier to be a catalyst, the dilution ratio is calculated based on the mass of the catalyst including the inert carrier. Hereinafter, a preferred embodiment will be described for the case of n=3 as an example. However, nature of the present invention is that when the reaction tube is divided by n in the gas flow direction to make catalyst layers, the filling length of catalyst layers except the nth catalyst layer with respect to the filling length of the nth catalyst layer is kept within a certain range. Therefore, a preferred embodiment is not limited to the case of n=3.

Upper layer (catalyst layer located closest to a gas inlet side for a raw material gas): a catalyst containing the catalytically active component represented by the formula (3) diluted to 50 mass % to 100 mass % with an inert substance is preferred, the catalyst diluted to 60 mass % to 100 mass % with an inert substance is more preferred, and the catalyst diluted to 70 mass % to 100 mass % with an inert substance is most preferred.

Middle layer (catalyst layer from the second layer to the (n−1)th layer from the gas inlet side for the raw material gas): a catalyst containing the catalytically active component represented by the formula (3) diluted to 80 mass % to 100 mass % with an inert substance is preferred, a catalyst diluted to 85 mass % to 100 mass % with an inert substance is more preferred, and a catalyst diluted to 90 mass % to 100 mass % with an inert substance is most preferred.

Lower layer (catalyst layer located on the nth layer from the gas inlet side for the raw material gas and located closest to the gas outlet side of the reaction tube): a catalyst diluted to 70 mass % to 100 mass % is preferred, a catalyst diluted to 75 mass % to 100 mass % is more preferred, and a catalyst diluted to 80 mass % to 100 mass % is most preferred. It is preferable to increase the activity of the lower layer, and the dilution ratio is most preferably 100 mass %.

In the case of providing 4 or more (n≥4) catalyst layers, middle layers are present, and the catalyst composition thereof may be changed, or the dilution ratio thereof may be changed within the above-mentioned range of the dilution ratio to form an additional layer.

Preferred embodiments of the present invention are the following 1) and 2).

1) n=2, the upper layer is a catalyst containing the catalytically active component represented by the formula (3), the dilution ratio is 100 mass %, and the Z component is cesium; the lower layer is a catalyst containing the catalytically active component represented by the formula (3), the Z component is potassium, and the dilution ratio is 100 mass %.

2) n=3, the middle layer is a catalyst containing the catalytically active component represented by the formula (3), the dilution ratio is 100 mass %, and the Z component is cesium; the upper layer is a catalyst obtained by diluting the catalyst in the middle layer with an inert substance; the lower layer is a catalyst containing the catalytically active component represented by the formula (3), the Z component is potassium, and the dilution ratio is 100 mass %.

Examples of the inert substance include known substances such as silica, alumina, titania, zirconia, niobia, silica alumina, silicon carbide, carbides, and mixtures thereof. Among these, silica, alumina, or a mixture thereof is preferred, silica and alumina are particularly preferred, and a mixture of silica and alumina is most preferred.

The shape of the inert substance is not limited, but is preferably a spherical shape, and the average particle size thereof is preferably 3 mm to 10 mm, and more preferably 3.5 mm to 9 mm. Particularly preferably, the average particle size is 4 mm to 8 mm.

Method for Producing Catalyst

The catalyst used in the present invention can be produced, for example, by the following steps a) to e).

Step a): Preparation

Usually, starting raw materials of respective elements constituting the catalytically active component are not limited. As a raw material of a molybdenum component, molybdenum oxides such as molybdenum trioxide, molybdic acid or salts thereof such as molybdic acid and an ammonium molybdate, molybdenum-containing heteropolyacids or salts thereof such as phosphomolybdic acid and silicomolybdic acid, and the like can be used. An ammonium molybdate is preferably used, and this allows for obtaining a high-performance catalyst. The ammonium molybdate includes plural kinds of compounds, such as ammonium dimolybdate, ammonium tetramolybdate and ammonium heptamolybdate, and among those in particular, the case of using ammonium heptamolybdate is the most preferred.

As a raw material of a bismuth component, bismuth salts such as bismuth nitrate, bismuth subcarbonate, bismuth sulfate and bismuth acetate, bismuth trioxide, metallic bismuth, and the like can be used. Bismuth nitrate is more preferable. In the case of using bismuth nitrate, a high-performance catalyst can be obtained. As for raw materials of iron, cobalt, nickel, and other elements, oxides thereof, or nitrates, carbonates, organic acid salts, hydroxides, and the like of iron, cobalt, nickel, and other elements, each of which may become an oxide of iron, cobalt, nickel, and other elements by strong heat, or mixtures of these can be usually used. For example, a raw material of the iron component and a raw material of the cobalt component and/or a raw material of the nickel component are dissolved in a desired proportion in water and are mixed under a condition at 10° C. to 80° C.; the mixture is mixed with an aqueous solution or slurry of the separately prepared raw material of the molybdenum component and the Z component under a condition at 20° C. to 90° C.; after heating and stirring the resulting mixture for about 1 hour under a condition at 20° C. to 90° C., an aqueous solution in which a raw material of the bismuth component is dissolved, and optionally a raw material of the X component and a raw material of the Y component are added into the resulting mixture, thereby obtaining an aqueous solution or slurry containing the catalyst components. Hereinafter, both are collectively referred to as a preparation liquid (A).

Here, the preparation liquid (A) is not always required to contain all of the constituent elements of the catalytically active component, and a part of those elements or a part of the amounts thereof may be added in the subsequent steps. In addition, on the occasion of preparing the preparation liquid (A), according to the amount of water for dissolving each of raw materials of the components, or in the case of adding an acid such as sulfuric acid, nitric acid, hydrochloric acid, tartaric acid and acetic acid for the purpose of dissolution, if the acid concentration enough for dissolution of the raw materials in the aqueous solution is not suitable for the preparation within a range of, for example, 5 mass % to 99 mass %, the form of the preparation liquid (A) is sometimes a clay-like lump. In this case, an excellent catalyst is not obtained. The form of the preparation liquid (A) is preferably an aqueous solution or slurry since an excellent catalyst is obtained.

Step b): Drying

Subsequently, the preparation liquid (A) obtained above is dried to form a dry powder. The drying method is not limited so long as it is a method in which the preparation liquid (A) can be completely dried. The examples thereof include drum drying, freeze drying, spray drying, and evaporation drying. Among these, spray drying, in which the slurry can be dried into a powder or granule within a short period of time, is particularly preferred in the present invention. The drying temperature of spray drying varies depending on the concentration of the slurry, the liquid sending speed, or the like. A temperature at the outlet of a drying machine is approximately 70° C. to 150° C. In addition, it is preferable to dry the obtained dry powder such that the average particle size thereof is 10 μm to 700 μm. Thus, a dry powder (B) is obtained.

Step c): Preliminary Calcination

Subjecting the obtained dry powder (B) to calcination at 200° C. to 600° C., preferably 300° C. to 600° C. under air circulation tends to improve molding properties, mechanical strength and performance of the catalyst. The calcination time is preferably 1 hour to 12 hours. In this manner, a preliminarily calcined powder (C) is obtained.

Step d): Molding

The molding method is not limited. In the case of molding the preliminary calcined powder (C) in a cylindrical or annular form, a method using a tablet molding machine, an extruder, or the like is preferred. Molding the preliminary calcined powder (C) in a spherical form is more preferred. The preliminarily calcined powder (C) may be molded in a spherical shape by using a molding machine and a method of carrying the preliminarily calcined powder (C) (including a molding aid and a strength improver, if desired) on an inert carrier such as ceramic is preferred. Here, as the carrying method, a tumbling granulation method, a method using a centrifugal flow coating apparatus, a wash coating method, and the like are widely known. The carrying method is not limited so long as the preliminarily calcined powder (C) can be carried uniformly on the carrier. However, in the case of taking into account the production efficiency of the catalyst and the performance of the prepared catalyst, a method in which using an apparatus having a flat or uneven disk in a bottom of a fixed cylindrical container, a carrier charged into the container is vigorously agitated by repeatedly performing rotation motion and revolution motion of the carrier itself by rotating the disk at a high speed, and the preliminarily calcined powder (C) and optionally a molding aid and/or a strength improver, are added into the container, thereby carrying the powder components on the carrier is more preferred.

For performing the carrying, it is preferred to use a binder. Specific examples of the binder which may be used include water, ethanol, methanol, propanol, a polyhydric alcohol, polyvinyl alcohol as a polymer-based binder, and a silica sol aqueous solution as an inorganic binder; ethanol, methanol, propanol, and a polyhydric alcohol are preferred; and a diol such as ethylene glycol and a triol such as glycerin is more preferred. Using an appropriate amount of a glycerin aqueous solution allows for improving the molding properties and obtaining a high-performance catalyst having good molding properties and high mechanical strength. Specifically, using an aqueous solution having a glycerin concentration of 5 mass % or more allows for obtaining a catalyst having a particularly high performance is obtained. The amount of such a binder to be used is typically 2 to 80 parts by mass based on 100 parts by mass of the preliminarily calcined powder (C). As the inert carrier, a carrier having a diameter of about 2 to 8 mm is usually used, and the preliminarily calcined powder (C) is carried thereon. The carrying rate is determined taking into account the condition of using the catalyst, for example, a reaction condition such as a space velocity of the reaction raw materials and raw material concentrations, and is typically 20 mass % to 80 mass %. Here, the carrying rate is expressed according to the following equation.

$$\text{Carrying rate (mass \%)} = 100 \times \left[ \frac{\text{mass of preliminarily calcined powder } (C) \text{ used for the molding}}{\left( \begin{array}{c} \text{mass of preliminarily calcined powder } (C) \\ \text{used for molding} + \text{mass of inert carrier} \\ \text{used for the molding} \end{array} \right)} \right] \quad (4)$$

Step e): Main Calcination

With respect to the molded body (D) obtained in step d), the catalytic activity and selectivity tend to improve by calcination at a temperature of 200° C. to 600° C. for about 1 to 12 hours. The calcination temperature is preferably 400° C. or higher and 600° C. or lower, and more preferably 500° C. or higher and 600° C. or lower. For the gas to be circulated, air is preferred on the grounds of its simpleness and easiness. Besides, nitrogen or carbon dioxide as an inert gas, or a nitrogen oxide-containing gas, an ammonia-containing gas, a hydrogen gas as a gas for producing a reducing atmosphere, or a mixture thereof can be also used. In this manner, a catalyst (E) is obtained.

Concentration of Alkene in Raw Material

The gas phase catalytic oxidation of the alkene in the present invention is carried out by introducing a mixed gas in which, as a composition of a raw material gas, 6 vol % to 12 vol % of an alkene (more preferably 6 vol % to 10 vol %), 5 vol % to 18 vol % of molecular oxygen, 0 vol % to 60 vol % of steam and 20 vol % to 70 vol % of an inert gas such as a mixed gas of nitrogen, carbon dioxide and the like are contained, onto the catalyst as prepared above at a temperature of from 250° C. to 450° C. under a pressure of atmospheric pressure to 10 atms, preferably atmospheric pressure to 5 atms, and more preferably atmospheric pressure to 3 atms for a contact time of 0.5 to 10 seconds.

In the present invention, the alkene includes alcohols that are converted into an alkene by an intramolecular dehydration reaction, such as tertiary butyl alcohol. It is preferred that a space velocity (reaction substrate supply rate (NL/hr)/catalyst filling space volume (L)) of the reaction substrate such as an alkene with respect to the volume of the catalyst is high from the viewpoint of production efficiency. However, when the space velocity is too high, the yield of the target product may decrease, and the life of the catalyst may be shortened. Therefore, in practice, the space velocity is preferably in the range of 40 to 200 $hr^{-1}$, and more preferably 60 to 180 $hr^{-1}$. Here, NL represents the volume of the reaction substrate in the standard conditions. The conversion rate of the alkene is preferably around the conversion rate at which the yield of acrolein can be obtained, and is usually 90% to 99.9%, preferably 95% to 99.5%, and more preferably 96% to 99%.

In the present invention, it is preferable to provide n catalyst layers in the flow direction of the raw material gas in the reaction tube and to locate the several kinds of the catalysts such that the activity become higher from the inlet for the raw material toward the outlet in the flow direction of the raw material gas. The number n of divisions is not limited, but is usually 2 to 5, and preferably 2 to 3.

In multi-layer filling, the filling length of the catalyst layer on the gas outlet side of the reaction tube is usually longer than the total filling length of the other catalyst layers. In this case, a catalyst having high activity is always set to be located at the gas outlet side in order to prevent heat generation on the gas inlet side. However, when the filling length of the catalyst having high activity on the outlet side is long, many disadvantages may occur. First, when the contribution of the catalyst having high activity in the reaction tube to the conversion rate increases, the raw material and the unsaturated aldehyde, which is the target product, undergo excessive oxidation, and the selectivity and yield of the target product decrease. Further, when the reaction becomes unstable due to disturbance factors or variations in various conditions, the longer filling length of the catalyst having high activity on the outlet side equates to the higher possibility of occurrence of the hot spots on the outlet side. This results in increasing the possibility of causing a runaway reaction. On the other hand, in the analysis of used catalysts in the industrial plant conducted by the inventor, among the catalysts filled in multiple layers, the catalyst layer on the gas inlet side is frequently deteriorated, and the catalyst on the gas outlet side of the reaction tube seldom deteriorates. Thus, the catalysts located from the gas inlet side of the reaction tube to the (n−1)th layer can influence the life of the catalyst filled in multiple layers.

When the catalyst layer on the gas outlet side of the reaction tube is shortened too much in order to obtain the effect of the present invention, the temperature of the reaction bath required to achieve the usual conversion rate and to obtain the target product rises too much by decrease in the activity of the entire catalyst layer. This increases the temperature of the hot spot on the (n−1)th layer from the inlet side to cause deterioration of the catalyst on the gas inlet side and deterioration of performance of the catalyst. In some cases, premature deterioration of the catalyst on the gas inlet side may cause intensive hot spots in the catalyst layer having high activity on the gas outlet side and may cause a sharp decrease in selectivity and yield of the target product. Therefore, it is also necessary to consider the balance of the catalysts on the gas inlet side and the gas outlet side such that the reaction bath temperature is prevented from rising excessively due to decrease in the activity of the entire catalyst layer by shortening the catalyst layer on the outlet side too much. The temperature of the reaction bath is appropriately set depending on the characteristics of the catalyst, the conditions of use, the required catalyst life, etc., and therefore the desired temperature cannot be unconditionally stated. The bath temperature at the initial stage of the reaction is preferably 350° C. or lower, and more preferably 340° C. or lower.

Performing the above production method in the industrial plant allows for improving the yield of the unsaturated aldehyde and preventing runaway on the gas outlet side in which the activity is high, and allows for achieving stable yield and operation in the industrial plant for a long period of time. This effect is considered to be derived from an increase of contribution of the catalyst having high selectivity to the reaction due to that the occupancy rate of the catalyst layer having a relatively high selectivity overtakes the occupancy rate of the catalyst layer having a relatively high selectivity.

EXAMPLES

Hereinafter, Examples will be shown with specific examples, but the present invention is not limited to Examples without departing from the spirit of the present invention.

In the following, the definition of the yield of acrolein is as follows.

$$\text{Yield of acrolein (mol \%)} = \left( \frac{\text{number of moles of acrolein produced/}}{\text{number of moles of supplied propylene}} \right) \times 100$$

With respect to the determination of L and/or Ln, the filling length ratio is preferable to be determined using an actually measured value instead of a design value. There are often a plurality of reaction tubes in a plant, and thus the average value obtained from measurement results of some reaction tubes can be used. The L and/or Ln can be calculated by, for example, filling the catalyst in order from an upper portion toward a lower portion of the reaction tube, and measuring the space length of the upper portion of each layer using a measure or the like.

Production Example: (Preparation of Catalyst)

While 3000 parts by mass of distilled water is heated and stirred, 423.7 parts by mass of ammonium molybdate and 0.73 parts by mass of potassium nitrate were dissolved in the distilled water to obtain an aqueous solution (A1). Separately, 378.4 parts by mass of cobalt nitrate, 139.6 parts by mass of nickel nitrate, and 161.6 parts by mass of ferric nitrate were dissolved in 1000 parts by mass of distilled water to obtain an aqueous solution (B1), and 97.1 parts by mass of bismuth nitrate was dissolved in 200 parts by mass of distilled water acidified by adding 81 parts by mass of concentrated nitric acid, to obtain an aqueous solution (C1). The aqueous solutions (B1) and (C1) were sequentially mixed with the above aqueous solution (A1) under vigorous stirring, and the resulting suspension was dried using a spray dryer and calcined at 440° C. for 6 hours, to obtain a preliminarily calcined powder (D2). At this time, the composition of the catalytically active component excluding oxygen was Mo=12, Bi=1.0, Ni=3.0, Fe=2.0, Co=6.5, K=0.05 in terms of atomic proportion.

Thereafter, the mass of the carrier and the preliminarily calcined powder used for the molding were adjusted so that a powder obtained by mixing 100 parts by mass of the preliminarily calcined powder (D2) with 5 parts by mass of crystalline cellulose is carried to an inert carrier (a spherical material with a diameter of 4.5 mm containing alumina and silica as main components) at 50 mass % of the carrying rate defined by the equation (4). Using a 20 mass % glycerin aqueous solution as a binder, the above mixture was carried and molded into a spherical shape having a diameter of 5.2 mm, to obtain a carried catalyst (E3). The carried catalyst (E3) was calcined at a calcination temperature of 530° C. for 4 hours in an air atmosphere to obtain a catalyst (F3). Further, in the same manner as the carried catalyst (E3), the above mixture was carried on a carrier having a diameter of 4.0 mm in a spherical shape such that the carrying rate was 50 mass %, to obtain a carried catalyst (E4) having a diameter of 4.7 mm. The carried catalyst (E4) was calcined at a calcination temperature of 530° C. for 4 hours to obtain a catalyst (F4).

A preliminarily calcined powder (D1) was obtained in the same manner as the above preliminarily calcined powder (D2), except for using cesium nitrate instead of potassium nitrate. In the obtained preliminarily calcined powder (D1), the composition of the catalytically active component excluding oxygen was Mo=12, Bi=1.0, Ni=3.0, Fe=2.0, Co=6.5, Cs=0.03 in terms of atomic proportion. The preliminarily calcined powder (D1) was carried and molded according to the method same as that of the carried catalyst (E3) to obtain a carried catalyst (E1). Further, the preliminarily calcined powder (D1) was carried on a carrier having a diameter of 4.5 mm in a spherical shape such that the carrying rate was 40 mass %, to obtain a carried catalyst (E2) having a diameter of 5.0 mm. The carried catalysts (E1) and (E2) were calcined at a calcination temperature of 530° C. for 4 hours in an air atmosphere to obtain catalysts (F1) and (F2), respectively.

Further, in the method for obtaining the preliminarily calcined powder (D1), the above mixing proportion was changed to make the composition of the catalytically active component excluding oxygen be Mo=12, Bi=0.7, Ni=2.5, Fe=2.0, Co=7.0, Cs=0.08 in terms of atomic proportion, to obtain a preliminarily calcined powder (D3). In the same manner as the carried catalyst (E3), the preliminarily calcined powders (D1) and (D3) were carried on a carrier having a diameter of 4.0 mm in a spherical shape such that the carrying rate was 50 mass %, to obtain carried catalysts (E5) and (E6) each having a diameter of 4.7 mm. The carried catalysts (E5) and (E6) were calcined at a calcination temperature of 530° C. for 4 hours in an air atmosphere to obtain catalysts (F5) and (F6), respectively.

Example 1

The oxidation reaction of propylene was carried out using the catalyst (F1) to the catalyst (F6) prepared as described above. The composition of the catalytically active component in the catalyst (F1) or (F2), which are used in Examples, on the inlet side of the reaction tube for the raw material gas is different from that in the catalyst (F3) or (F4), which are used in Examples, on the outlet side of the reaction tube for the raw material gas. The composition of the catalytically active component in the catalyst (F1) to (F4) falls within the range of the composition described in the general formula (3).

Silica alumina spheres having a diameter of 5.2 mm were filled for 20 cm of a stainless steel reactor, from the inlet side of the stainless steel reactor for a raw material gas having an inner diameter of 25 mm, in which a jacket for circulating a molten salt as a heat medium and a thermocouple for measuring the temperature of the catalyst layer was installed on the tube axis. Then, in a gas outlet direction, the upper layer (raw material gas inlet side) was filled for 80 cm of the reactor with a diluted catalyst (diluted to 85 mass %) in which the catalyst (F1) and a silica-alumina mixture-inert spherical carrier were mixed at a mass ratio of 85:15, the middle layer was filled for 110 cm of the reactor with the catalyst (F1) without dilution, and the lower layer was filled for 160 cm of the reactor with the catalyst (F3) without dilution sequentially. Accordingly, a catalyst layer having a three-layer structure and L/Ln of 1.19 was formed. The temperature of the reaction bath was set to 315° C., and the supply amounts of propylene, air, water, and nitrogen were set to be propylene:oxygen (oxygen contained in the supplied air):water:nitrogen (nitrogen supplied separately from air)=1:1.7:1:2.4 in terms of the molar proportion for the raw materials. The propylene concentration (vol %) in the supplied raw materials was $1/(1+(1.7/0.21)+1+2.4) \times 100 = 8$ vol %. The method of obtaining the propylene concentration (vol %) in the supplied raw materials in Examples 2 and 4 described later is the same as that of this Example. The oxidation reaction of propylene was carried out by circulating the supplied raw materials such that the space velocity of propylene was 100 $hr^{-1}$, setting the pressure on the outlet side of the reaction tube during the flow of all gas to 50 kPaG, and changing the temperature of the reaction bath when 300 hours had passed since the reaction started. As a result of examining the reaction result after changing the temperature of the reaction bath, the yield of acrolein was the highest value at 318° C., and the propylene conversion rate and the temperature of the hot spot of each catalyst layer at the temperature were obtained. The results are shown in Table 1. As the temperature of the hot spot in Table 1, the temperature in the hot spot of each catalyst layer is described.

Example 2

Under the conditions of the oxidation reaction in Example 1, the upper layer was filled for 200 cm of the reactor with the catalyst (F2) without dilution, and in the outlet direction for the raw material gas, the lower layer was sequentially filled for 150 cm of the reactor with the catalyst (F4) without dilution to form a catalyst layer having a two-layer structure and L/Ln of 1.33. The oxidation reaction of propylene was carried out in the same manner as in Example 1, except that the supply amounts of propylene, air, water, and nitrogen were set to be propylene:oxygen (oxygen contained in the supplied air):water:nitrogen (nitrogen supplied separately from air)=1:2.0:0.7:4.0 in terms of the molar proportion for the raw materials, the supplied raw materials were circulated such that the space velocity of propylene was 170 $hr^{-1}$ and the pressure on the outlet side of the reaction tube during the flow of all gas was set to 75 kPaG to start the reaction. As a result of examining the reaction result after changing the temperature of the reaction bath, the yield of acrolein was the highest value at 335° C., and the propylene conversion rate and the temperature of the hot spot of each catalyst layer at the temperature were obtained. The results are shown in Table 1.

Example 3

The oxidation reaction of propylene was carried out in the same manner as in Example 1, except that under the conditions of the oxidation reaction in Example 2, the upper layer was filled for 200 cm of the reactor with the catalyst (F5) without dilution, and in the outlet direction of the raw material gas, the lower layer was sequentially filled for 150 cm of the reactor with the catalyst (F6) without dilution to form a catalyst layer having a two-layer structure. In Example 3, L/Ln was 1.33. As a result of examining the reaction result after changing the temperature of the reaction bath, the yield of acrolein was the highest value at 328° C., and the propylene conversion rate and the temperature of the hot spot of each catalyst layer at the temperature were obtained. The results are shown in Table 2.

Comparative Example 1

The oxidation reaction of propylene was carried out in the same manner as in Example 1, except that under the conditions of the oxidation reaction in Example 1, the middle layer was filled for 80 cm of the reactor with the catalyst (F1) without dilution, and the lower layer was filled for 190 cm of the reactor with the catalyst (F3) without dilution. In Comparative Example 1, L/Ln was 0.84. As a result of examining the reaction result after changing the temperature of the reaction bath, the yield of acrolein was the highest value at 318° C., and the propylene conversion rate and the temperature of the hot spot of each catalyst layer at the temperature were obtained. The results are shown in Table 2.

Comparative Example 2

The oxidation reaction of propylene was carried out in the same manner as in Example 2, except that under the conditions of the oxidation reaction in Example 2, the upper layer was filled for 150 cm of the reactor with the catalyst (F2) without dilution, and the lower layer was filled for 200 cm of the reactor with the catalyst (F4) without dilution. In Comparative Example 2, L/Ln was 0.75. As a result of examining the reaction result after changing the temperature of the reaction bath, the yield of acrolein was the highest value at 330° C., and the propylene conversion rate and the temperature of the hot spot of each catalyst layer at the temperature were obtained. The results are shown in Table 1.

For the case of providing a catalyst layer consisting of three layers (n=3), the test conditions and results were summarized in Table 1 and for the case of providing a catalyst layer consisting of two layers (n=2), the test conditions and results were summarized in Table 2. Usually, in an oxidation reaction for obtaining an unsaturated aldehyde or an unsaturated carboxylic acid by circulating a reaction gas containing molecular oxygen and using a fixed bed catalyst, as described in the present application, the greater the space velocity of the raw material such as propylene, what is called the load on the catalyst, becomes, the higher the productivity becomes. On the other hand, it is known that along with this, selectivity and yield of target product tend to be impaired to a certain degree. Therefore, it is common to compare the performance in regions where loads applied to the catalyst are the same level, such as a space velocity. Further, for example, even when the yield decreases by about 0.5% due to an increase in load, if the operation can be performed with twice the load, the target product can be obtained at about twice the speed. Therefore, if it is possible to operate with a high load, the production efficiency can be greatly improved.

velocity of propylene was 80 $hr^{-1}$, setting the pressure on the outlet side of the reaction tube during the flow of all gas to 0 kPaG, and changing the temperature of the reaction bath when 300 hours had passed since the reaction started. As a result of examining the reaction result after changing the temperature of the reaction bath, the yield of acrolein was the highest value at 315° C., and the propylene conversion rate and the temperature of the hot spot of each catalyst layer at the temperature were obtained. The results are shown in Table 3. As the temperature of the hot spot in Table 3, the temperature of the hot spot of each catalyst layer is described.

Example 5

The oxidation reaction was carried out under the same conditions as in Example 4, except that the upper layer (F2)

TABLE 1

| | Space velocity of propylene ($hr^{-1}$) | Temperature of reaction bath (° C.) | Highest yield of acrolein (%) | Propylene conversion rate (%) | L (cm) | Ln (cm) | L/Ln | Temperature of the hot spot (%) Upper layer Middle layer Lower layer |
|---|---|---|---|---|---|---|---|---|
| Example 1 | 100 | 318 | 84.6 | 95.3 | 190 | 160 | 1.19 | 383 370 363 |
| Comparative Example 1 | 100 | 318 | 83.9 | 96.5 | 160 | 190 | 0.84 | 381 366 367 |

TABLE 2

| | Space velocity of propylene ($hr^{-1}$) | Temperature of reaction bath (° C.) | Highest yield of acrolein (%) | Propylene conversion rate (%) | L (cm) | Ln (cm) | L/Ln | Temperature of the hot spot (%) Upper layer Lower layer |
|---|---|---|---|---|---|---|---|---|
| Example 2 | 170 | 335 | 83.8 | 96.0 | 200 | 150 | 1.33 | 387 368 |
| Example 3 | 170 | 328 | 84.0 | 95.2 | 200 | 150 | 1.33 | 374 353 |
| Comparative Example 2 | 170 | 330 | 83.2 | 96.7 | 150 | 200 | 0.75 | 380 369 |

Example 4

Silica alumina spheres having a diameter of 5.2 mm were filled for 2 cm of a stainless steel reactor, from the inlet side for the raw material gas of the stainless steel reactor having an inner diameter of 28.4 mm and a thermocouple installed on the tube axis for measuring the temperature of the catalyst layer. Then, in a gas outlet direction, the upper layer (raw material gas inlet side) was filled for 56.5 mm of the reactor with the catalyst (F2) without dilution, and the lower layer was filled for 43.5 mm of the reactor with the catalyst (F4) without dilution sequentially. Accordingly, a catalyst layer having a two-layer structure and L/Ln of 1.30 was formed. The oxidation reaction of propylene was carried out by setting the temperature of the reaction bath to 320° C., setting the supply amounts of propylene, air, water and nitrogen to be propylene:oxygen:water:nitrogen=1:2.0:0.7:4.0 in terms of the molar proportion for the raw materials, circulating the supplied raw materials such that the space was filled for 71.4 mm of the reactor and the lower layer (F4) was filled for 28.6 mm of the reactor. The results are shown in Table 3.

Comparative Example 3

The oxidation reaction was carried out under the same conditions as in Example 4, except that the upper layer (F2) was filled for 77.8 mm of the reactor and the lower layer (F4) was filled for 22.2 mm of the reactor. The results are shown in Table 3.

Comparative Example 4

The oxidation reaction was carried out under the same conditions as in Example 4, except that catalysts (4), (5) and (6) described in Example 3 of JP-A-H10-168003 (Patent Literature 5) were produced, and the catalyst was filled with catalysts (4), (5) and (6) for a filling length of 28.25 mm, 28.25 mm and 43.5 mm in this order from the inlet side of the raw material gas. The results are shown in Table 3.

TABLE 3

| | Space velocity of propylene (hr$^{-1}$) | Temperature of reaction bath (° C.) | Highest yield of acrolein (%) | Propylene conversion rate (%) | L (mm) | Ln (mm) | L/Ln | Temperature of the hot spot (%) Upper layer Middle layer Lower layer |
|---|---|---|---|---|---|---|---|---|
| Example 4 | 80 | 315 | 84.9 | 95.3 | 56.5 | 43.5 | 1.30 | 386 — 381 |
| Example 5 | 80 | 330 | 82.5 | 93.8 | 71.4 | 28.6 | 2.50 | 400 — 378 |
| Comparative Example 3 | 80 | 335 | 82.5 | 93.7 | 77.8 | 22.2 | 3.50 | 408 — 374 |
| Comparative Example 4 | 80 | 320 | 82.4 | 96.7 | 56.5 | 43.5 | 1.30 | 418 419 395 |

As confirmed from the results in Table 3, in Example 4 in which catalyst layers having different compositions of the catalytically active components in the upper layer and the lower layer were filled to be L/Ln=1.30, the maximum yield of acrolein was high, the temperature of the reaction bath was kept low, and, furthermore, the temperature of the hot spot of the upper layer could be decreased. Thus, it was confirmed that the oxidation reaction could be stably carried out for a long period of time with a high yield. Similarly, in Example 5 in which catalyst layers having different compositions of the catalytically active components in the upper layer and the lower layer are filled to be L/Ln=2.50, the temperature of the reaction bath and the temperature of the hot spot of the upper layer could be kept low. In contrast, in Comparative Example 3 in which catalyst layers are filled to be L/Ln=3.50, the yield of acrolein could not be increased unless the temperature of the reaction bath was increased, and therefore the temperature of the hot spot of the upper layer was also increased. Further, in Comparative Example 4 in which the same composition of the catalytically active components was included in all of the upper layer, the middle layer, and the lower layer, the temperature of the hot spot of the upper layer was very high even when the temperature of the reaction bath was lowered.

Although the present invention has been described in detail with reference to specific examples, it is apparent to those skilled in the art that it is possible to add various alterations and modifications without departing from the spirit and the scope of the present invention.

The present application is based on Japanese Patent Application (No. 2019-065494) filed on Mar. 29, 2019, the entire contents of which are incorporated herein by reference. In addition, all references cited here are entirely incorporated.

INDUSTRIAL APPLICABILITY

The present invention allows for achieving the effect to improve the yield and prevent the reaction runaway in a plant for producing an unsaturated aldehyde. This enables stable operation with stable yield in an industrial plant for a long period of time.

The invention claimed is:

1. A method for producing an unsaturated aldehyde comprising,
subjecting an alkene to partial oxidation using a fixed bed multi-tube reactor to produce the corresponding unsaturated aldehyde,
wherein n catalyst layers in a gas flow direction in a reaction tube is provided, n being 2 or more,
when a filling length of the catalyst layers from a first catalyst layer to an (n−1)th catalyst layer from a gas inlet side of the reaction tube is L, and a filling length of an nth catalyst layer from the gas inlet side of the reaction tube is Ln, a relationship between L and Ln satisfies the following equation (1):

$$1 < L/Ln \leq 3, \qquad (1)$$

a composition of a catalytically active component contained in the catalyst layers from the first catalyst layer to the (n−1)th layer from the gas inlet side of the reaction tube is different from a composition of a catalytically active component contained in the nth catalyst layer from the gas inlet side of the reaction tube, and each catalyst layer in the reaction tube contains a catalyst containing a catalytically active component having a composition represented by the following formula (3):

$$Mo_{12}Bi_aFe_bCo_cNi_dX_eY_fZ_gO_h \qquad (3)$$

where X is at least one element selected from the group consisting of magnesium (Mg), calcium (Ca), manganese (Mn), copper (Cu), zinc (Zn), cerium (Ce) and samarium (Sm), Y is at least one element selected from the group consisting of boron (B), phosphorus (P), arsenic (As), antimony (Sb) and tungsten (W), Z is at least one element selected from the group consisting of sodium (Na), potassium (K), rubidium (Rb) and cesium (Cs), (a) to (g) represent an atomic proportion of each component, h is a numerical value determined by a degree of oxidation of a catalyst component, a=0.40 to 2.0, b=1 to 3, c=3 to 7.5, d=2 to 4, e=0 to 10, f=0 to 10, g=0.01 to 0.50, h is a numerical value for satisfying oxidation states of the other elements, d/a is 1 or more and 9 or less, d/g is 5 or more and 350 or less, and a/g is 0.8 or more and 90 or less.

2. The method for producing an unsaturated aldehyde according to claim 1, wherein the relationship between L and Ln satisfies the following equation (2):

$$1.1 < L/Ln \leq 1.4. \tag{2}$$

3. The method for producing an unsaturated aldehyde according to claim 1, wherein a catalyst contained in the catalyst layer has a spherical shape.

4. The method for producing an unsaturated aldehyde according to claim 1, wherein a concentration of the alkene in a raw material is 6 vol % to 12 vol %.

5. The method for producing an unsaturated aldehyde according to claim 1, wherein a catalyst contained in the nth catalyst layer is not diluted with an inert substance.

6. The method for producing an unsaturated aldehyde according to claim 1, wherein a catalyst contained in the catalyst layer is a carried catalyst.

* * * * *